(12) United States Patent
Welmaker et al.

(10) Patent No.: US 6,414,144 B1
(45) Date of Patent: Jul. 2, 2002

(54) PROCESS FOR PREPARATION OF CYCLOPENTA[B][1,4]DIAZEPINO[6,7,1-HI] INDOLE DERIVATIVES

(75) Inventors: Gregory Scott Welmaker, Jackson; Joan Eileen Sabalski, Yardville, both of NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/016,435

(22) Filed: Nov. 2, 2001

Related U.S. Application Data

(60) Provisional application No. 60/245,915, filed on Nov. 3, 2000.

(51) Int. Cl.⁷ ............................................. C07D 243/00
(52) U.S. Cl. ...................................................... 540/555
(58) Field of Search ......................................... 540/555

(56) References Cited

U.S. PATENT DOCUMENTS 3,914,250 A  * 10/1975 Kim ........................... 260/315

OTHER PUBLICATIONS

Gregory E. Martin et al., J. Med. Chem., 1989, 1052–1056, 32.
J.L. Browning et al., Society for Neuroscience Abstracts, Oct. 1999, 2075, 25(2), Abstract 830.12.
Jackson B. Hester et al., J. Med. Chem., 1970, 827–835, 13.
Dong H. Kim, J. Heterocycl. Chem., 1976, 1187–1192, 13(6).

* cited by examiner

Primary Examiner—Brenda Coleman
Assistant Examiner—C. Style
(74) Attorney, Agent, or Firm—Rebecca R. Barrett

(57) ABSTRACT

The present invention provides processes for the preparation of 1, 2, 3, 4, 8, 9, 10, 10a-octahydro-7bH-cyclopenta[b][1,4]diazepino[6, 7, 1-hi]indole derivatives of the general formula:

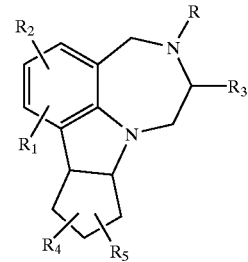

wherein: R is H, alkyl, acyl, or aroyl; $R_1$, $R_2$, $R_4$ and $R_5$ are H, OH, alkyl, cycloalkyl, alkoxy s, halogen, fluorinated alkyl, —CN, —NH—$SO_2$-alkyl, —$SO_2$—NH-alkyl, alkyl amide, amino, alkylamino s, dialkylamino, fluorinated alkoxy, acyl, aryl, or aroyl; $R_3$ is H, alkyl, cycloalkyl, alkoxy, fluorinated alkyl, —NH—$SO_2$-alkyl, —$SO_2$—NH-alkyl, alkyl amide, amino, alkylamino, dialkylamino, fluorinated alkoxy, acyl, aryl, or aroyl; or a pharmaceutically acceptable salt thereof, which are useful in the treatment of central nervous system disorders.

9 Claims, No Drawings

PROCESS FOR PREPARATION OF CYCLOPENTA[B][1,4]DIAZEPINO[6,7,1-HI] INDOLE DERIVATIVES

This application claims benefit of provisional application Ser. No. 60/245,915, filed Nov. 3, 2000, the entire disclosure of which is hereby incorporated by reference.

The present invention relates to a process for the preparation of 1, 2, 3, 4, 8, 9, 10, 10a-octahydro-7bH-cyclopenta[b][1,4]diazepino[6,7,1-hi]indole derivatives and intermediates thereof, the final products being useful in the treatment of central nervous system disorders, including obsessive-compulsive disorder, depression, anxiety, generalized anxiety disorder, schizophrenia, panic disorder, migraine, sleep disorders, such as sleep apnea, eating disorders, such as hyperphagia, obesity, epilepsy, and spinal cord injury.

BACKGROUND OF THE INVENTION

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the $21^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J. ) 147–210 (Wiley-Liss, N.Y., 1991).] The $5HT_{2C}$ receptor (formerly called the $5HT_{1C}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558–564 (1988).] Studies in several animal species and in humans have shown that the non-selective $5HT_{2C}$ receptor agonist, meta-chlorophenylpiperazine (MCPP) decreases food intake. [Cowen, P. J., Clifford, E. M. , Williams, C., Walsh, A. E. S., Fairburn, C. G. *Nature* 376: 557 (1995).] Tecott, et al have demonstrated that transgenic mice lacking the $5HT_{2C}$ receptor eat more and are heavier than Wild Type mice. [Tecott, L. H., Sun, L. M., Akana, S. F., Strack, A. M., Lowenstein, D. H., Dallman, M. F., Jullus, D. *Nature* 374: 542–546 (1995).] Compounds of this invention are $5HT_{2C}$ receptor subtype selective agonists which are selective over other monoamine receptors, causes a reduction in food intake and result in a reduction in weight gain. Other therapeutic indications for $5HT_{2C}$ agonists are obsessive compulsive disorder, depression, panic disorder, schizophrenia, sleep disorders, eating disorders, and epilepsy.

The non-selective $5\text{-}HT_{2C}$ agonist, meta-chlorophenylpiperazine (m-CPP), has been shown to block conditioned avoidance responding (CAR) in the rat, an activity usually associated with antipsychotic activity in man [Martin, Gregory E.; Elgin, Jr., Robert J.; Mathiasen, Joanne R.; Davis, Coralie B.; Kesslick, James M.; Baldy, William J.; Shank, Richard P.; DiStefano, Deena L.; Fedde, Cynthia L.; Scott, Malcolm K. *J. Med. Chem.* 1989, 32, 1052–1056]. More recently, additional data suggests that $5\text{-}HT_{2C}$ agonism may produce an antipsychotic-like effect in the CAR model [Browning, J. L.; Young, K. A.; Hicks, P. B. Presented at the $29^{th}$ Annual Meeting of the Society for Neuroscience, Miami Beach, Fla., October 1999, Abstract 830.12].

U.S. Pat. No. 3,914,250 (Oct. 21, 1975) describes 1,4-diazepino[6,5,4-jk]carbazoles, having the structures below, as anticonvulsant agents.

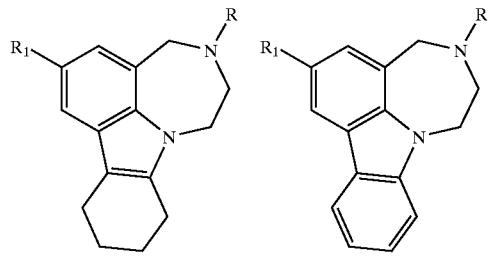

Pyrrolo[3,2,1-jk][1,4]benzodiazepines and 4,5-dihydropyrrolo[3,2,1-jk][1,4]-benzodiazepines have been described by Hester et aL (*J. Med. Chem.* 1970, 13, 827–835) to have central nervous system activity.

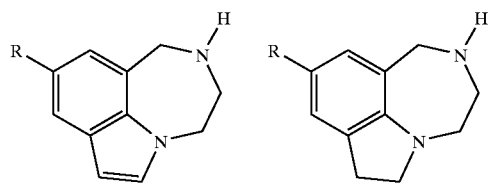

DESCRIPTION OF THE INVENTION

The present invention provides processes for the preparation of 1, 2, 3, 4, 8, 9, 10, 10a-octahydro-7bH-cyclopenta[b][1,4]diazepino[6, 7,1-hi]indole derivatives of the general formula:

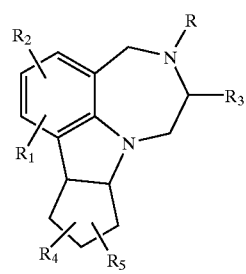

I wherein:
R is hydrogen, alkyl of 1–6 carbon atoms, acyl of 2–7 carbon atoms, or aroyl;
$R_1$, $R_2$, $R_4$ and $R_5$ are each, independently, hydrogen, hydroxy, alkyl of 1–6 carbon atoms, cycloalkyl, alkoxy of 1–6 carbon atoms, halogen, fluorinated alkyl of 1–6 carbon atoms, —CN, —NH—$SO_2$-alkyl of 1–6 carbon atoms, —$SO_2$—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, aryl, or aroyl;
$R_3$ is hydrogen, alkyl of 1–6 carbon atoms, cycloalkyl, alkoxy of 1–6 carbon atoms, fluorinated alkyl of 1–6 carbon atoms, —NH—$SO_2$-alkyl of 1–6 carbon atoms, —$SO_2$—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, aryl, or aroyl;
or a pharmaceutically acceptable salt thereof.

The definitions above of fluorinated alkyl and fluorinated alkoxy groups indicate the specified alkyl or alkoxy groups having any amount of fluorine substitution including, but not limited to, groups such as —CHF$_2$, —CF$_3$, —C$_2$F$_5$, —OCF$_3$, etc.

The compounds of this invention may contain an asymmetric carbon atom and some of the compounds of this invention may contain one or more asymmetric centers and may thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

The term "alkyl" includes both straight- and branched-chain saturated aliphatic hydrocarbon groups. The term "aroyl" is defined as an aryl ketone, where aryl is defined as an aromatic system of 6–14 carbon atoms, which may be a single ring or multiple aromatic rings fused or linked together as such that at least one part of the fused or linked rings forms the conjugated aromatic system. Preferred aryl groups include phenyl, naphthyl, biphenyl, anthryl, tetrahydronaphthyl, phenanthryl groups. Halogen is defined as F, Cl, Br, and I.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. The processes herein will be understood to include an optional additional step of forming a salt form of the products via standard addition reactions with any pharmaceutically acceptable organic or inorganic acid.

Preferred compounds prepared by the processes of this invention are those in which R is hydrogen. Another preferred group of compounds of this invention are those in which R and R$_3$ are hydrogen and R$_1$, R$_2$, R$_4$ and R$_5$ are as defined above. In another group of compounds herein, R, R$_3$, R$_2$, and R$_5$ are hydrogen and R$_1$ and R$_4$ are as defined above. A further group comprises compounds wherein R, R$_1$, R$_2$, R$_3$, and R4 are hydrogen and R$_5$ is as defined above. In a final group R, R$_1$, R$_2$, R$_3$, R$_4$ and R$_5$ are each hydrogen.

The 5HT$_{2C}$ receptor agonists of this invention are useful for the treatment or prevention in mammals, preferably in humans, of disorders involving the central nervous system such as obsessive-compulsive disorder, depression, atypical depression, bipolar disorders, anxiety, generalized anxiety disorder, schizophrenia, psychoses, personality disorders, organic mental disorders, behavioral disorders associated with dementia or age-related conditions, aggressivity, drug and alcohol addiction, social phobias, sexual dysfunction, panic disorder, migraine, steep disorders, such as sleep apnea, eating disorders, such as hyperphagia, bulimia or anorexia nervosa, obesity, epilepsy, and premenstrual tension.

This invention also includes methods of utilizing the compounds herein in treatments or preventitive regimens for treatment of central nervous system deficiencies associated with trauma, stroke, neurodegenerative diseases or toxic or infective CNS disorders including, but not limited to, encephalitis or menengitis; or cardiovascular disorders, including thrombosis; gastrointestinal disorders such as malfunction of gastrointestinal motility; and diabetes insipidus. These methods include the improvement or inhibition of further degradation of central nervous system activity during or following the malady or trauma in question. Included in these improvements are maintenance or improvement in motor and motility skills, control, coordination and strength.

A process of this invention comprises a method of preparing a compound of the formula:

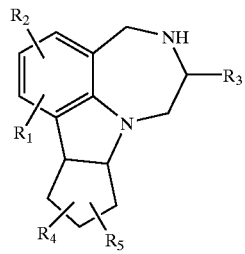

wherein R, R$_1$, R$_2$, R$_3$, R$_4$ and R$_5$ are as defined above, the process comprising the steps of:

a) reacting an optionally substituted cyclopentaindole-5-carboxylic acid of the formula III with an amino acid ester of formula IV, wherein R' represents an alkyl group of from 1 to 10 carbon atoms, to produce an optionally substituted cyclopentaindole-5-carbonyl-amino acetic acid alkyl ester of formula V;

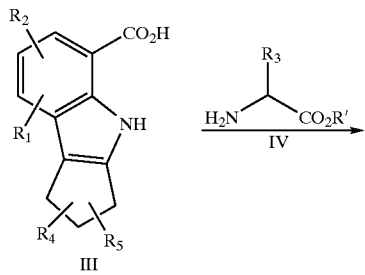

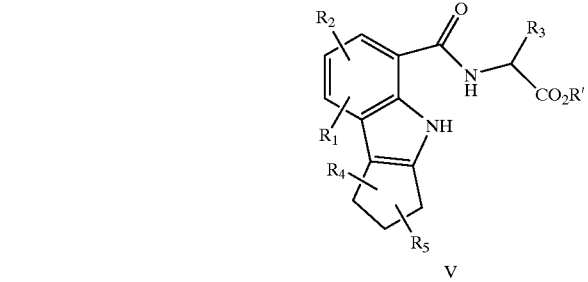

b) treating the optionally substituted cyclopentaindole-5-carbonyl-amino acetic acid alkyl ester of formula V from step a) with a reducing agent to provide an optionally substituted cyclopenta[b]indole-5-carbonyl-amino-acetic acid alkyl ester of the formula VI:

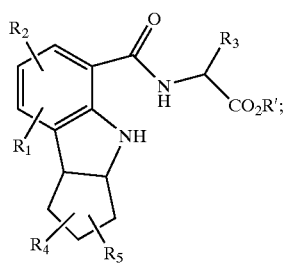

c) hydrolysing the reduced ester compound of formula VI in the presence of a base, followed by treatment with an acid, to form an optionally substituted diaza-benzo[cd]lcyclopenta[a]azulene-4,7-dione compound of formula VII:

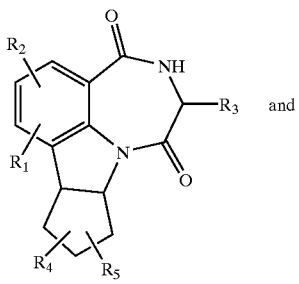

d) treating the optionally substituted diaza-benzo[cd] cyclopenta[a]azulene-4,7-dione compound of formula VII with a reducing agent to provide a compound of the formula VIII:

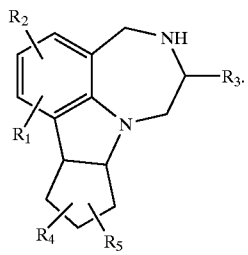

The process described above further comprises an optional step of treating the compound of formula VIII with an alkylating agent or an acylating agent to provide a compound of the formula:

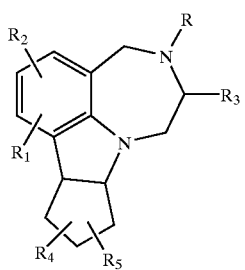

wherein R is hydrogen, alkyl of 1–6 carbon atoms, acyl of 2–7 carbon atoms, or aroyl; and $R_1$, $R_2$, $R_3$, R4 and $R_5$ are as defined above.

This process also comprises an optional step of treating a compound of Formula VII or Formula I with a pharmaceutically acceptable organic or inorganic acid to form a corresponding pharmaceutically acceptable addition salt form of the compound of Formulas VII or I.

Compounds of formula I are new compounds. In Scheme I and in the following description and examples the process steps are explained in detail. A 2-hydrazinobenzoic acid I is allowed to react with a ketone II under standard Fischer-indole conditions. The reaction is carried out in the presence of an acid, such as sulfuric acid or acetic acid, with or without a solvent, such as water or ethanol, at a temperature above ambient temperature, such as 30–150° C.

The resulting indole-carboxylic acid III is coupled with an amino acid ester IV, such as L-alanine methyl ester, in the presence of peptide coupling reagents, such as 1-(3-dimethylaminopropyl)-3-ethylcarbodiimide hydrochloride (EDC) and 1-hydroxybenzotriazole hydrate (HOBt), and a base, such as diisopropylethylamine, in an inert organic solvent, such as dichloromethane. It will be understood that the amino acid ester IV may comprise any known in the art to be used in cyclization procedure as disclosed in Scheme 1. Among the most preferred are those wherein R' in formula IV are represent alkyl groups of from 1 to 10 carbon atoms, either straight, branched or cyclic. Among the most preferred are the shorter chain esters, such as the methyl, ethyl, isopropyl, n-propyl, n-butyl, and t-butyl esters.

The resulting indole-amide V can be reduced to indoline-amide VI using conventional reduction methods, for instance by catalytic hydrogenation in the presence of a metal catalyst, such as 5% Pd/C, or by a hydride source, such as triethylsilane or borane, in the presence of an acid, such as trifluoroacetic acid.

The indoline-amide VI can be cyclized to the bislactam VII by hydrolysis of the ester with a base, such as lithium hydroxide, and subsequent treatment with an acid, such as acetic acid.

Scheme 1

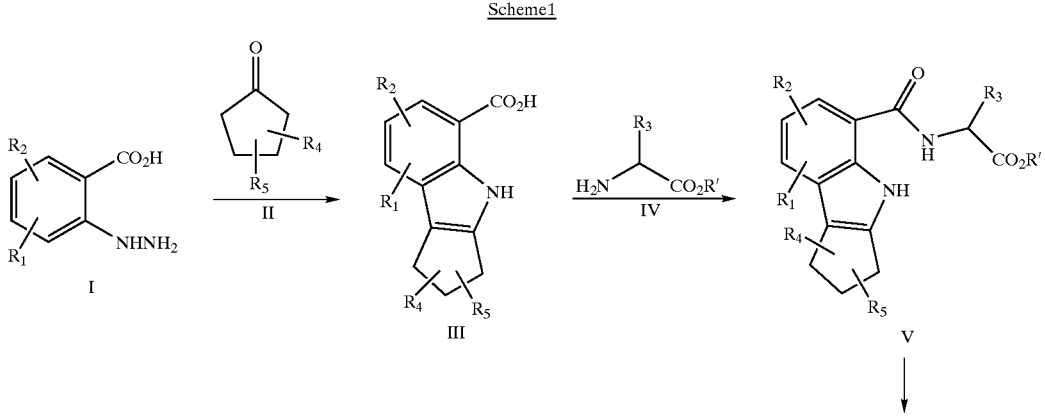

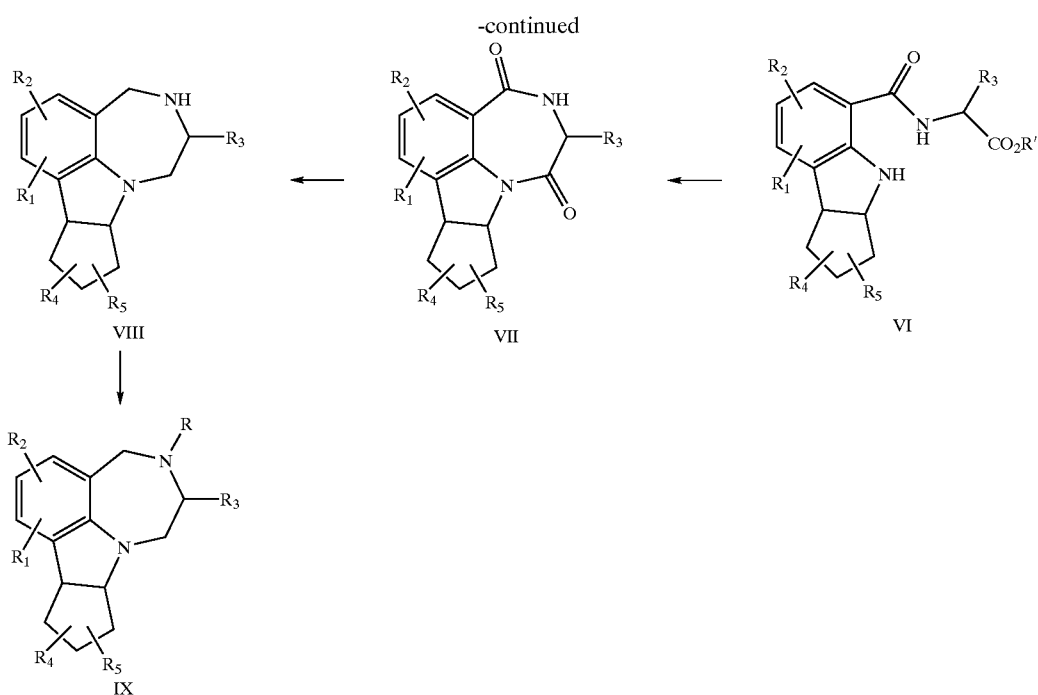

The bislactam VII can be reduced to the benzodiazepine VIII with a reducing agent, such as borane or lithium aluminum hydride, in the presence of an inert organic solvent, such as tetrahydrofuran.

Reaction of benzodiazepine VIII with an alkyl halide, such as methyl iodide, or an acyl halide, such as acetyl chloride, or an aroyl chloride, such as benzoyl chloride, gives IX.

The acylation steps of this invention are understood to include reactions of the appropriate compound with any acylating agent and reaction conditions known in the art. Useful in these steps are acylating agents include acid halides and esters or anhyrides of the appropriate aliphatic carboxylic acid. Useful acid halides include acetyl chloride, propionyl chloride, isobutyryl chloride, benzoyl chloride, etc. Acid anhydrides include acetic anhydride and benzoic anhydride. Similarly, alkylation steps herein are understood to include any relevant alkylating agents and conditions known in the art. These include, but are not limited to the use of alkyl halides, such as methyl iodide, or alkyl tosylates or aldehyde alkylating agents in the presence of an applicable reducing agent.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids. The processes herein will be understood to include an optional additional step of forming a salt form of the products via standard addition reactions with any pharmaceutically acceptable organic or inorganic acid.

A method of resolving the (R,R) enantiomer from racemic mixtures of these compounds comprises the steps of:

a) dissolving about 1 equivalent of the racemic compound mixture of a product of this invention in a solubilizing amount of an alcohol resolving agent at a temperature of from about 50° C. to the reflux temperature for the alcohol, preferably between about 50° C. and 70° C., under an inert atmosphere, to create a resolving solution;

b) treating the resolving solution of step a) with from about 0.1 to about 0.35 equivalents of dibenzoyl-L-tartaric acid, preferably from about 0. 15 equivalents to about 0.3 equivalents, more preferably from about 0.23 to about 0.27 equivalents, most preferably about 0.25 equivalents to precipitate the desired (R,R) enantiomer from the resolving solution as the corresponding tartaric acid salt form; and c) separating the desired enantiomer from the resolving solution through conventional means, such as filtration.

It will be understood that this process may be followed by additional steps of filtration and purification to enhance the purity and yield of the desired enantiomer product in question.

In step b) it is preferred that the temperature of the resolving solution be maintained at a temperature at or above about 50° C., preferably nearer to the reflux temperature of the alcohol in question. The alcohol component of step a) may be comprise a single alcohol or a combination of two or more alcohols selected from those known in the art into which the compound in question can be dissolved. Among the preferred alcohols are the commercially available and relatively low boiling alcohols comprising 10 carbon atoms or less including methanol, ethanol, n-propanol, isopropanol, n-butanol, t-butanol, cyclohexanol, etc.

It will also be understood that the (S,S) enantiomer of the racemic mixture mentioned above could then be purified and collected from the remaining resolving solution described above after collection of the (R,R) tartaric acid salt.

An analogous method for resolving the (S,S) enantiomer from the racemic mixtures of compounds of this invention, the method comprising the steps a) through c) listed above, with dibenzoyl-D-tartaric acid being used in place of dibenzoyl-L-tartaric acid in step b). Comparably, the (R,R) enantiomer can be collected and purified by conventional means from the remaining solution after the tartaric acid salt

EXAMPLE 1

(2S)-(rel-7bR, 10aR)-2-Methyl-1.2,3,4,8,9,10,10a-Octahydro-7bH-Cyclopenta[b][1,4]Diazepino[6,7.1-hi]Indole

A. 1,2,3,4-Tetrahydrocyclopenta[b]Indole-5-Carboxylic Acid

To a stirred solution of 2-hydrazinobenzoic acid hydrochloride (53 mmol, 10.0 g) and cyclopentanone (58 mmol, 4.9 g) in 1,4-dioxane (100 mL) was added dropwise concentrated $H_2SO_4$ (~18M, 63 mmol, 3.5 mL). The resulting solution was heated to reflux for 2 hours. $^1H$ NMR analysis of a crude aliquot indicated complete reaction. The reaction was allowed to cool to room temperature and then concentrated to dryness to give a red solid which was used without further purification.

$^1H$ NMR (DMSO-$d_6$, 300 MHz) δ 10.8(s, 1H), 7.6–7.0(m, 3H), 2.8(m, 4H), 2.4(m, 2H).

B. Ethyl (2S)-2-[(1,2,3,4-Tetrahydrocyclopenta[b]Indol-5-ylcarbonyl)Amino]-Propanoate To a stirred, cooled (0° C.) solution of crude 1,2,3,4-tetrahydrocyclopenta[b]indole-5-carboxylic acid (60 mmol, 12 g), L-alanine ethyl ester (72 mmol, 11 g), 1-[3-(dimethylamino)propyl]-3-ethylcarbodiimide hydrochloride (EDC) (72 mmol, 14 g), 1-hydroxybenzotriazole (HOBT) (72 mmol, 10 g) in $CH_2Cl_2$ (100 mL) was slowly added diisopropylethylamine (360 mmol, 46 g). The reaction mixture was stirred overnight while warming to room temperature. The reaction was concentrated in vacuo and the resulting oil was partitioned between water and ethyl acetate. The organic layer was washed with saturated aqueous $NH_4Cl$, $NaHCO_3$, and brine, dried over $MgSO_4$, filtered and concentrated to a brown oil. The crude material was purified by chromatography through silica gel (Biotage) eluting with 15% ethyl acetate-hexanes to afford a yellow oil (8.4 mmol, 2.5 g, 14%).

$^1H$ NMR (DMSO-$d_6$, 300 MHz) δ 10.9(s, 1H), 8.74(d, 1H), 7.62(d, 1H), 7.48(d, 1H), 6.98(t, 1H), 4.47(t, 1H), 4.08(m, 2H), 2.75(m, 4H), 2.40(m, 2H), 1.42(d, 3H), 1.15(t, 3H).

C. Ethyl (2S)-2-[(1,2,3,3a,4,8b-Hexahydrocyclopenta[b]Indol-5-ylcarbonyl)-Amino]Propanoate A solution of ethyl (2S)-2-[(1,2,3,4-tetrahydrocyclopenta[b]indol-5-ylcarbonyl)amino]propanoate (8.4 mmol, 2.5 g) in ethanol (40 mL) was added to a mixture of 5% palladium on carbon (2 g) in ethanol (2 mL). Concentrated hydrochloric acid (10 mL) was added and the resulting mixture was hydrogenated at 45 psi for 4 hours. The reaction mixture was filtered through Celite. The filter bed was washed well with ethanol and the combined filtrates were concentrated. The resulting oil was partitioned between 1 N NaOH and ethyl acetate. The orgainc phase was dried over $MgSO_4$, filtered and concentrated to yield an oil (1.9 g, 6.1 mmol, 73%).

$^1H$ NMR (DMSO-$d_6$, 300 MHz) δ 8.7($m_1$ H), 7.63(m, 1H), 7.25(m, 1H), 6.85(m, 2H), 4.40(m, 2H), 4.10(m, 2H), 3.76(m, 1H), 1.90(m, 2H), 1.68(m, 3H), 1.38(d, 3H), 1.31(m, 1H), 1.16(t, 3H).

D. (2S)-2-[(1,2,3,3a,4,8b-Hexahydrocyclopenta[b]Indol-5-ylcarbonyl)Amino]-Propanoic Acid A 1 M aqueous lithium hydroxide solution (13 mmol, 13 mL) was added to a solution of ethyl (2S)-2-[(1,2,3,3a,4,8b-hexahydrocyclopenta[b]indol-5-ylcarbonyl)amino] propanoate (6.1 mmol, 1.9 g) in THF (50 mL). The reaction mixture was stirred at room temperature for 18 h. The reaction was concentrated in vacuo and diluted with 0.1 N HCI and ethyl acetate. The phases were separated and the organic phase was washed with water, dried over $MgSO_4$, filtered, and concentrated to give a yellow oil (1.6 g, 6.1 mmol, quantitative).

$^1H$ NMR (DMSO-$d_6$, 300 MHz) δ 12.4(s, 1H), 8.21(d, 1H), 7.43(m, 1H), 7.01(d, 1H), 6.70(br s, 1H), 6.40(t, 1H), 4.35(m, 2H), 3.63(t, 1H), 1.88(m, 2H), 1.62(m, 4H), 1.30(d, 3H).

E. (2S)-2-Methyl-2,3,8,9,10,10a-Hexahydro-7bH-Cyclopenta[b][1,4]Diazepino-[6,7,1-hi]Indole-1,4-Dione A solution of (2S)-2-[(1,2,3,3a,4,8b-hexahydrocyclopenta[b]indol-5-ylcarbonyl)amino]propanoic acid (6.1 mmol, 1.6 g) was dissolved in acetic acid (50 mL) and heated to reflux for 18 h. The reaction was allowed to cool to room temperature and was concentrated to dryness. The crude material was purified by flash column chromatography (silica gel; 1:1 ethyl acetate-hexanes) to provide two diastereomers: less polar product (0.88 mmol, 0.23 g, 14%) and more polar product (0.18 mmol, 45 mg, 3%). The mixed fractions were also collected to provide another 3.9 mmol (1.0 g, 64%) of material.

Less Polar Product (A)

$^1H$ NMR (DMSO-$d_6$, 300 MHz) δ 8.2(d, 1H), 7.61(m, 1H), 7.46(dd, 1H), 7.16(t, 1H), 4.86(dt, 1H), 3.87(m, 2H), 1.92(m, 2H), 1.75(m, 1H), 1.58(m, 2H), 1.26(d, 3H), 1.06(m, 1H).

F. (2S)-(rel-7bR,10aR)-2-Methyl-1,2,3,4,8,9,10,10a-Octahydro-7bH-Cyclopenta[b][1,4]Diazepino[6,7,1-hi]Indole A mixture of diastereomers of (2S)-2-methyl-2,3,8,9,10,10a-hexahydro-7bH-cyclopenta[b][1,4]diazepino[6,7,1-hi]indole-1,4-dione (3.9 mmol, 1.0 g) was suspended in 1 M $BH_3$.THF (15 mL) and heated to reflux for 18 h. After cooling to room temperature, the solution was quenched with methanol and concentrated. The resulting solid was suspended in 1 N NaOH and stirred at room temperature for 1 h. The aqueous phase was then extracted with chloroform and the combined extracts were dried over $MgSO_4$, filtered, and concentrated to give a yellow solid (3.5 mmol, 0.80 g, 90%). Flash chromatography through silica gel (gradient elution 5%-10% methanol-chloroform) afforded the two diastereomers. The less polar product was arbitrarily assigned the R,R configuration and the more polar product the S,S configuration.

Anal. Calcd. for $C_{15}H_{20}N_2$. 1.5 mol $H_2O$: C, 70.56; H, 9.08; N, 10.97. Found: C, 70.24; H, 9.58; N, 10.81. MS ((+))APCI, m/e (%)) 229(100, [M+H]$^+$). IR (solid ATR, cm$^{-1}$) 2960, 2880, 2310, 1460, 1440, 1210, 1160, 1120, 1090, 1070.

$^1H$ NMR (DMSO-$d_6$, 400 MHz) δ 7.32(t, J=7.56 Hz, 1H), 7.22(d, J=7.3 Hz, 1H), 7.12(d, J=7.3 Hz, 1H), 4.35(m, 1H), 4.07(m, 2H), 3.82(d, J=16.84 Hz, 1H), 3.62(m, 1H), 3.14(dd, J=8.54 Hz, 10.74 Hz, 1H), 3.0(m, 1H), 2.04–1.69(m, 4H), 1.51(m, 2H), 1.22(d, J=6.6 Hz, 4H). [α]$_D$+99 (c. 0.11, DMSO).

EXAMPLE 2

(2S)-(rel-7bS,10aS)-2-Methyl-1,2,3,4,8,9,10,10a-Octahydro-7bH-Cyclopenta[b][1,4]Diazepino[6,7,1-hi]Indole

Following the procedure of method 1F, the more polar material provided the product which was assigned the S,S configuration. Anal. Calcd. for $C_{15}H_{20}N_2$. 1.1 mol $H_2O$: C, 72.60; H, 9.02; N, 11.29. Found: C, 72.63; H, 8.80; N, 10.95. MS ((+)APCI, m/e (%)) 229(100, [M+H]$^+$). $^1$H NMR (DMSO-d$_6$, 400 MHz) δ 6.86(d, J=7.3 Hz, 1H), 6.73(d, J=7.3 Hz, 1H), 6.52(t, J=7.4 Hz, 1H), 3.95(m, 2H), 3.82(d, J=15.86 Hz, 1H), 3.61(m, 1H), 3.41(dd, J=3.17 Hz, 13.4 Hz, 2H), 3.21(m, 1H), 2.83(dd, J=3.9 Hz, 13.2 Hz, 1H), 1.94(m, 1H), 1.77(m, 1H), 1.55(m, 4H), 1.15(d, J=6.6 Hz, 3H). [α]$_D$+38 (c. 0.10, DMSO).

EXAMPLE 3

(2R)-(rel-7bR,10aR)-2-Methyl-1,2,3,4,8,9,10,10a-Octahydro-7bH-Cyclopenta[b][1,4]Diazepino[6,7,1-hi]Indole A. Methyl (2R)-2-[(1,2,3,4-Tetrahydrocyclopenta[b]Indol-5-ylcarbonyl)Amino]-Propanoate Following the procedure of method 1B, employing D-alanine methyl ester (64 mmol, 8.9 g) afforded a yellow oil (4.9 mmol, 1.4 g, 8%). $^1$H NMR (DMSO-d$_6$, 300 MHz) δ 10.8(s, 1H), 8.78(d, 1H), 7.61(d, 1H), 7.49(d, 1H), 7.0(t, 1H), 4.5(m, 1H), 3.63(s, 3H), 2.76(m, 4H), 2.42(m, 2H), 1.42(d, 3H).

B. Methyl (2R)-2-[(1,2,3,3a,4,8b-Hexahydrocyclopenta[b]Indol-5-ylcarbonyl)-Amino]Propanoate Following the procedure of method 1C, methyl (2R)-2-[(1,2,3,4-tetrahydrocyclopenta[b]indol-5-ylcarbonyl)amino]propanoate (4.9 mmol, 1.4 g) was hydrogenated using 5% Pd/C (1.5 g) and concentrated HCl (7 mL) in methanol (25 mL) to yield an oil (2.7 mmol, 0.77 9, 55%).

$^1$H NMR (DMSO-d$_6$, 300 MHz) δ 8.34(d, 1H), 7.44(d, 1H), 7.02(d, 1H), 6.70(s, 1H), 6.41(t, 1H), 4.39(m, 2H), 3.65(m, 1H), 3.60(s,3H), 1.89(m, 1H), 1.61(m, 4H), 1.35(d, 3H), 1.29(m, 1H).

C. (2R)-2-[(1,2,3,3a,4,8b-Hexahydrocyclopenta[b]Indol-5-ylcarbonyl)Amino]-Propanoic Acid Following the procedure of method 1D, methyl (2R)-2-[(1,2,3,3a,4,8b-hexahydrocyclopenta[b]indol-5-ylcarbonyl)amino]propanoate (2.7 mmol, 0.77 g) was hydrolyzed to the acid using 1 M aqueous lithium hydroxide (5.9 mL) in THF (20 mL) to yield an orange oil which was used without further purification.

$^1$H NMR (DMSO-d$_6$, 300 MHz) δ 12.4(br s, 1H), 8.2(d, 1H), 7.43(d, 1H), 7.01(d, 1H), 6.9(br s, 1H), 6.4(t, 1H), 4.33(m, 2H), 3.62(t, 1H), 1.89(m, 2H), 1.61(m, 4H), 132(d, 3H).

D. (2R)-2-Methyl-2,3,8,9,10,10a-Hexahydro-7bH-Cyclopenta[b]-[1,4]Diazepino-[6,7,1-hi]Indole-1,4-Dione Following the procedure of method 1E, (2R)-2-[(1,2,3,3a,4,8b-hexahydrocyclopenta[b]indol-5-ylcarbonyl)amino]propanoic acid was cyclized by refluxing in acetic acid (50 mL). Purification by flash chromatography through silica gel (elution with 5% methanol-chloroform) provided each diastereomer: less polar product (1.5 mmol, 0.39 g, 56% over 2 steps) arbitrarily assigned as the R,R configuration and more polar product (0.47 mmol, 0.11 g, 17% over 2 steps) assigned as the S,S configuration.

Less Polar Product (A)

$^1$H NMR (DMSO-d$_6$, 300 MHz) δ 8.2(d, 1H), 7.62(d, 1H), 7.46(d, 1H), 7.16(t, 1H), 4.87(m, 1H), 3.88(m, 2H), 1.94(m, 3H), 1.76(m, 1H), 1.59(m, 2H), 1.28(d, 3H).

E. (2R)-(rel-7bR,10aR)-2-Methyl-1,2,3,4,8,9,10,10a-Octahydro-7bH-Cyclopenta[b][1,4]Diazepino[6,7,1-hi]Indole Following the procedure of method 1F, (2R)-(rel-7bR, 10aR)-2-methyl-2,3,8,9,10,10a-hexahydro-7bH-cyclopenta[b]-[1,4]diazepino[6,7,1-hi]indole-1,4-dione (1.5 mmol, 0.39 g) was reduced with 1 M BH$_3$.THF (10 mL) to yield a yellow solid (0.47 mmol, 0.11 g, 31%).

Anal. Calcd. for C$_{15}$H$_{20}$N$_2$. 0.15 mol H$_2$0: C, 77.98; H, 8.86; N, 12.12. Found: C, 77.72; H, 9.03; N, 11.89. MS ((+)ESI, m/e(%)) 457(17, [2M+H]$^+$), 307(81, [M+H+DMSO]$^+$), 229(100, [M+H]$^+$). IR (solid ATR, cm$^{-1}$) 3240, 2950, 2870, 1590,1460, 1350,1290,1270, 740. $^1$H NMR (DMSO-d$_6$, 400 MHz) δ 6.8(d, J=7.1 Hz, 1H), 6.65(d, J=7.1 Hz, 1H), 6.47(t, J=7.3 Hz, 1H), 3.94(m, 1H), 3.80, 3.71 (ABq, J$_{AB}$=16.1 Hz, 2H), 3.59(m 1H), 3.35(dd, J=3.17 Hz, 12.93 Hz, 1H), 3.02(m, 1H), 2.75(dd, J=4.39 Hz, 12.93 Hz, 1H) 2.49(m, 1H), 1.94(m, 1H), 1.76(m, 1H), 1.56(m, 4H), 1.07(d, J=6.6 Hz, 3H). [α]$_D$−82 (c. 0.10, DMSO).

EXAMPLE 4

(2R)-(rel-7bS,10aS)-2-Methyl-1,2,3,4,8,9,10,10a-Octahydro-7bH-Cyclopenta[b][1,4]Diazepino[6,7,1-hi]Indole Following the procedure of method 1F, (2R)-(rel-7bS, 10aS)-2-methyl-2,3,8,9,10,10a-hexahydro-7bH-cyclopenta[b]-[1,4]diazepino[6,7,1-hi]indole-1,4-dione (0.47 mmol, 0.11 9g) was reduced with 1 M BH$_3$.THF (8 mL) to yield the product (0.27 mmol, 61 mg, 57%). MS ((+)APCI, m/e (%)) 457(20, [2M+H]$^+$), 229(100, [M+H]$_+$). $^1$H NMR (DMSO-d$_6$, 400 MHz) δ 6.85(d, J=7.08 Hz, 1H), 6.72(d, J=7.3 Hz, 1H), 6.52(t, J=7.3 Hz, 1H), 3.82(dd, J=5.6 Hz, 9.0 Hz, 1H), 3.79, 3.51(ABq, J$_{AB}$=15.1 Hz, 2H), 3.70(dt, J=2.9 Hz, 9.0 Hz, 1H), 3.28(m, 1H), 3.06(dd, J=2.1 Hz, 12.1 Hz, 1H), 2.78(m, 1H), 2.43(m, 1H), 1.92–1.30(m, 6H), 1.02(d, J=6.6 Hz, 3H).

EXAMPLE 5

(2R,7bS,10aS)-1,2,3,4,8,9,10,10a-Octahydro-7bH-Cyclopenta[b][1,4]Diazepino[6,7,1-hi]Indol-2-ylmethanol A. Methyl (2S)-3-Hydroxy-2-[(1,2,3,4-Tetrahydrocyclopenta[b]Indol-5-ylcarbonyl)Amino]Propanoate Following the procedure of method 1B, employing L-serine methyl ester (64 mmol, 9.9 g) afforded a yellow solid (8.9 mmol, 2.7 g, 14%).

$^1$H NMR (DMSO-d$_6$, 300 MHz) δ 10.8(s, 1H), 8.51(d, 1H), 7.61(d, 1H), 7.51(d, 1H), 7.01(t, 1H), 5.08(m, 1H), 4.56(q, 1H), 3.82(d, 2H), 3.62(s, 3H), 2.76(m, 4H). 2.42(m, 2H).

B. Methyl (2S)-2-[(1,2,3,3a,4,8b-Hexahydrocyclopenta[b]Indol-5-ylcarbonyl)Amino)-3-Hydroxypropanoate Following the procedure of method 1C, methyl (2S)-3-hydroxy-2-[(1,2,3,4-tetrahydrocyclopenta[b]indol-5-ylcarbonyl)amino]propanoate(8.9 mmol, 2.7 g) was hydrogenated using 5% Pd/C (2 g) and concentrated HCl (10 mL) in methanol (25 mL) to yield the crude product (8.9 mmol, 2.7 g, quantitative).

$^1$H NMR (DMSO-d$_6$, 300 MHz) δ 8.3(d, 1H), 7.86(d, 1H), 7.34(d, 1H), 7.03(t, 1H), 5.80(br s, 2H), 4.45(m, 2H), 3.80(m, 2H), 3.61 (s, 3H), 2.0–1.55(m, 6H).

B. (2S)-2-[(1,2,3,3a,4,8b-Hexahydrocyclopenta[b]Indol-5-ylcarbonyl]Amino}-3-Hydroxypropanoic Acid Following the procedure of method 1D, methyl (2S)-2-[(1,2,3,3a,4,8b-hexahydrocyclopenta[b]indol-5-ylcarbonyl) amino]-3-hydroxypropanoate (8.9 mmol, 2.7 g) was hydrolyzed to the acid using 1 M aqueous lithium hydroxide (40 mL) in THF (40 mL) to yield a red oil (1.5 mmol, 430 mg, 17%).

$^1$H NMR (DMSO-d$_6$, 300 MHz) δ 7.92(d, 1H), 7.40(d, 1H), 7.03(d, 1H), 6.43(t, 1H), 4.39(m, 2H), 3.63(br m, 4H), 2.0–1.2(m, 6H).

C. (2S)-2-(Hydroxymethyl)-2,3,8,9,10,10a-Hexahydro-7bH-Cyclopenta[b][1,4]-Diazepino[6,7,1-hi]Indole-1,4-Dione Following the procedure of method 1E, (2S)-2-[(1,2,3,3a,4,8b-hexahydrocyclopenta[b]indol-5-ylcarbonyl)amino]-3-hydroxypropanoic acid (1.5 mmol, 430 mg) was cyclized by refluxing in acetic acid (40 mL). Purification by flash chromatography through silica gel (elution with 5% methanol-chloroform) provided each diastereomer: less polar product (0.55 mmol, 0.15 g, 37%) arbitrarily assigned as the R,R configuration and more polar product (0.26 mmol, 0.070 g, 17%) assigned as the S,S configuration.

Less Polar Product (A)

$^1$H NMR (DMSO-$d_6$, 300 MHz) δ 8.44(d, 1H), 7.63(d, 1H), 7.48(d, 1H), 7.19(m, 1H), 4.88(m,1H), 4.39(dd, 1H), 4.22(t, 1H), 4.07(m, 1H), 3.91 (m, 1H), 2.0–1.5(m, 6H).

D. (2R)-rel-7bS,10aS)-1,2,3,4,8,9,10,10a-Octahydro-7bH-Cyclopenta[b][1,4]-Diazepino[6,7,1-hi]Indol-2-ylmethanol Following the procedure of method 1F, (2S)-(rel-7bS,10aS)-2-hydroxymethyl-2,3,8,9,10,10a-hexahydro-7bH-cyclopenta[b]-[1,4]diazepino[6,7,1-hi]indole-1,4-dione (0.26 mmol, 0.070 g) was reduced with 1 M BH$_3$.THF (1 mL) to yield a solid (0.17 mmol, 0.046 g, 65%).

MS ((+)APCI, m/e(%)) 323(35, [M+H+DMSO]$^+$, 245 (100, [M+H]$^+$). $^1$H NMR (DMSO-$d_6$, 400 MHz) δ 6.85(d, J=7.1 Hz, 1H), 6.73(d, J=7.3 Hz, 1H), 6.52(t, J=7.3 Hz, 1H), 4.70(m, 1H), 3.86, 3.50(ABq, $J_{AB}$=14.9 Hz, 2H), 3.85(m, 1H), 3.70(dt, J=2.9 Hz, 9.0 Hz, 1H), 3.35(m, 1H), 3.22(m, 2H), 2.64(m, 1H), 2.40(m, 1H), 1.90(m, 1H), 1.75(m, 1H), 1.60(m, 2H), 1.50(m, 1H), 1.40(m, 2H).

What is claimed is:

1. A process for producing compounds of the formula:

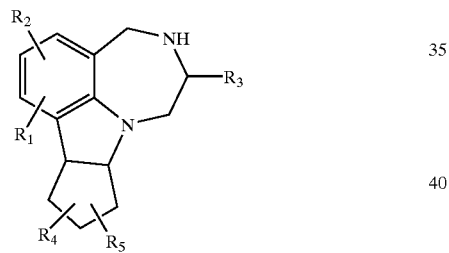

wherein:

R$_1$, R$_2$, R$_4$ and R$_5$ are each, independently, hydrogen, hydroxy, alkyl of 1–6 carbon atoms, cycloalkyl, alkoxy of 1–6 carbon atoms, halogen, fluorinated alkyl of 1–6 carbon atoms, —CN, —NH—SO$_2$-alkyl of 1–6 carbon atoms, —SO$_2$—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, aryl, or aroyl;

R$_3$ is hydrogen, alkyl of 1–6 carbon atoms, cycloalkyl, alkoxy of 1–6 carbon atoms, fluorinated alkyl of 1–6 carbon atoms, —NH—SO$_2$-alkyl of 1–6 carbon atoms, —SO$_2$—NH-alkyl of 1–6 carbon atoms, alkyl amide of 1–6 carbon atoms, amino, alkylamino of 1–6 carbon atoms, dialkylamino of 1–6 carbon atoms per alkyl moiety, fluorinated alkoxy of 1–6 carbon atoms, acyl of 2–7 carbon atoms, aryl, or aroyl;

the process comprising the steps of:

a) reacting an optionally substituted cyclopentaindole-5-carboxylic acid of the formula III with an amino acid ester IV, wherein R' represents an alkyl group of from 1 to 10 carbon atoms, to produce an optionally substituted cyclopentaindole-5-carbonyl-amino acetic acid alkyl ester of formula V;

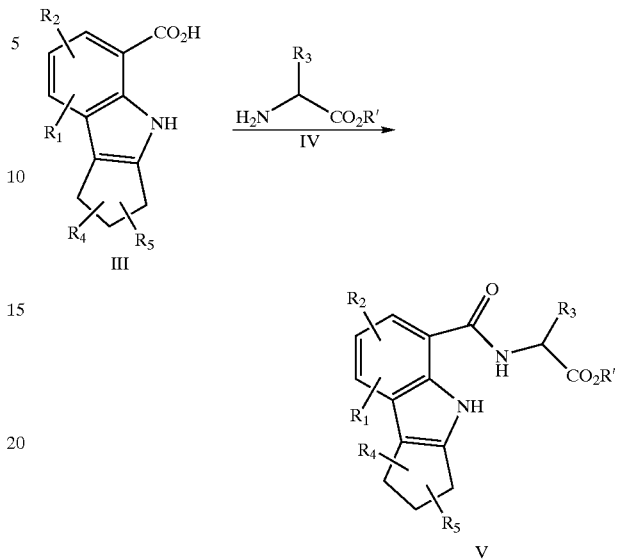

b) treating the optionally substituted cyclopentaindole-5-carbonyl-amino acetic acid alkyl ester of formula V from step a) with a reducing agent to provide an optionally substituted cyclopenta[b]indole-5-carbonyl-amino-acetic acid alkyl ester of the formula VI:

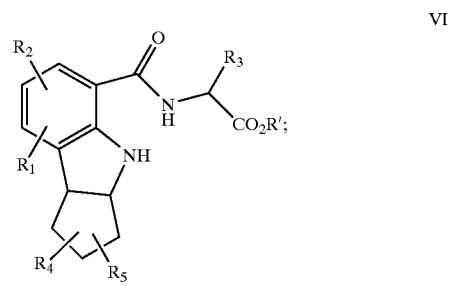

c) hydrolysing the reduced ester compound of formula VI in the presence of a base, followed by treatment with an acid, to form an optionally substituted diaza-benzo[cd]cyclopenta[a]azulene-4,7-dione compound of formula VII:

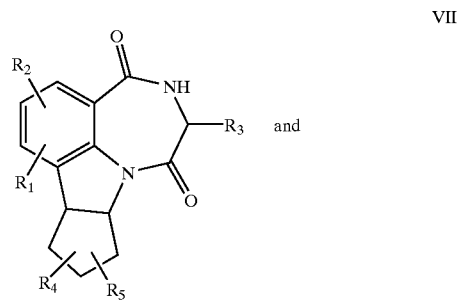

and d) treating the optionally substituted diaza-benzo[cd]cyclopenta[a]azulene-4,7-dione compound of formula VII with a reducing agent to provide a compound of the formula:

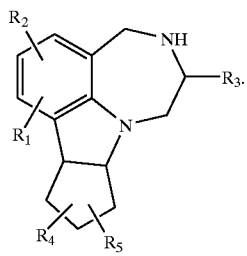

2. The process of claim 1 further comprising the step of treating the compound of the formula:

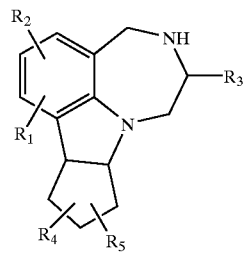

wherein $R_1, R_2, R_3, R_4$ and $R_5$ are as defined in claim 1, with a pharmaceutically acceptable inorganic or organic acid to provide a pharmaceutically acceptable salt thereof.

3. The process of claim 2 wherein the pharmaceutically acceptable inorganic or organic acid is selected from the group of acetic acid, propionic acid, lactic acid, citric acid, tartaric acid, succinic acid, fumaric acid, maleic acid, malonic acid, mandelic acid, malic acid, phthalic acid, hydrochloric acid, hydrobromic acid, phosphoric acid, nitric acid, sulfuric acid, methanesulfonic acid, napthalenesulfonic acid, benzenesulfonic acid, toluenesulfonic acid, or camphorsulfonic acid.

4. The process of claim 1 further comprising the step of treating the compound of the formula:

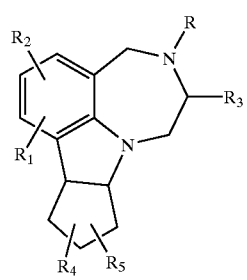

with an alkylating agent to provide a compound of the formula:

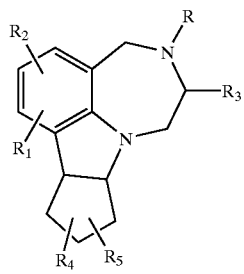

wherein R is alkyl of 1–6 carbon atoms; and $R_1, R_2, R_3, R_4$ and $R_5$ are as defined in claim 1.

5. The process of claim 4 further comprising the step of treating the compound of the formula:

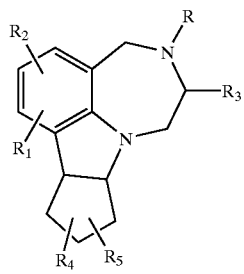

wherein R, $R_1, R_2, R_3, R_4$ and $R_5$ are as defined in claim 4, with a pharmaceutically acceptable inorganic or organic acid to provide a pharmaceutically acceptable salt thereof.

6. The process of claim 5 wherein the pharmaceutically acceptable inorganic or organic acid is selected from the group of acetic acid, propionic acid, lactic acid, citric acid, tartaric acid, succinic acid, fumaric acid, maleic acid, malonic acid, mandelic acid, malic acid, phthalic acid, hydrochloric acid, hydrobromic acid, phosphoric acid, nitric acid, sulfuric acid, methanesulfonic acid, napthalenesulfonic acid, benzenesulfonic acid, toluenesulfonic acid, or camphorsulfonic acid.

7. The process of claim 1 further comprising the step of treating the compound of the formula:

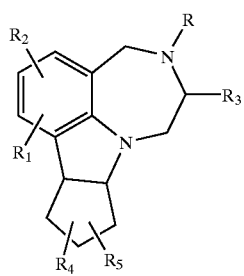

with an acylating agent to provide a compound of the formula:

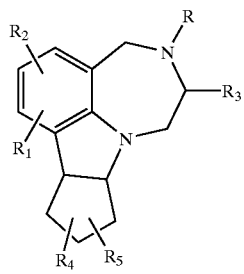

wherein R is acyl of 2–7 carbon atoms, or aroyl; and $R_1, R_2, R_3, R_4$ and $R_5$ are as defined in claim 1.

8. The process of claim 7 further comprising the step of treating the compound of the formula:

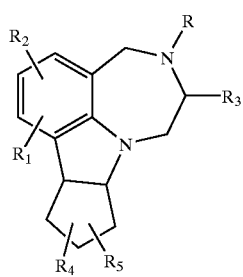

wherein R, $R_1$, $R_2$, $R_3$, $R_4$ and $R_5$ are as defined in claim 7, with a pharmaceutically acceptable inorganic or organic acid to provide a pharmaceutically acceptable salt thereof.

9. The process of claim 8 wherein the pharmaceutically acceptable inorganic or organic acid is selected from the group of acetic acid, propionic acid, lactic acid, citric acid, tartaric acid, succinic acid, fumaric acid, maleic acid, malonic acid, mandelic acid, malic acid, phthalic acid, hydrochloric acid, hydrobromic acid, phosphoric acid, nitric acid, sulfuric acid, methanesulfonic acid, napthalenesulfonic acid, benzenesulfonic acid, toluenesulfonic acid, or camphorsulfonic acid.

* * * * *